US011464817B2

(12) United States Patent
Jeong et al.

(10) Patent No.: US 11,464,817 B2
(45) Date of Patent: Oct. 11, 2022

(54) COMPOSITION FOR PREVENTING, IMPROVING OR TREATING FEMALE MENOPAUSAL DISEASE

(71) Applicant: NINE B CO., LTD., Daejeon (KR)

(72) Inventors: Seon-Yong Jeong, Yongin-si (KR); Eunkuk Park, Suwon-si (KR)

(73) Assignee: NINE B CO., LTD., Daejeon (KR)

( * ) Notice: Subject to any disclaimer, the term of this patent is extended or adjusted under 35 U.S.C. 154(b) by 76 days.

(21) Appl. No.: 16/803,968

(22) Filed: Feb. 27, 2020

(65) Prior Publication Data
US 2020/0276255 A1    Sep. 3, 2020

(30) Foreign Application Priority Data
Feb. 28, 2019    (KR) .................. 10-2019-0023859

(51) Int. Cl.
*A61K 36/185*    (2006.01)
*A61P 5/30*    (2006.01)
*A61K 36/40*    (2006.01)

(52) U.S. Cl.
CPC ............ *A61K 36/185* (2013.01); *A61K 36/40* (2013.01); *A61P 5/30* (2018.01); *A61K 2236/333* (2013.01)

(58) Field of Classification Search
None
See application file for complete search history.

(56) References Cited

U.S. PATENT DOCUMENTS

| | | | |
|---|---|---|---|
| 2005/0214244 A1* | 9/2005 | Fleming | A61K 36/73 424/74 |
| 2006/0222721 A1* | 10/2006 | Cohen | A61P 25/24 424/741 |
| 2007/0269541 A1* | 11/2007 | Rohdewald | A61K 36/15 424/766 |
| 2008/0069909 A1* | 3/2008 | Olalde | A61K 36/488 424/728 |

FOREIGN PATENT DOCUMENTS

CN    101621996 A    *    1/2010    ............... A61K 8/60

OTHER PUBLICATIONS

CN-101621996-A translated doc (Year: 2010).*
Shin (Corni fructus ameliorates menopause symptom in 4-vinylcyclohexen diepoxide, Mol Cell Toxicol (2018) 14:35-42) (Year: 2018).*
Naoki Nanashima et al., "Phytoestrogenic activity of blackcurrant (*Ribes nigrum*) anthocyanins is mediated through astrogen receptor alpha", Molecular Nutrition Food Research, 2015, vol. 59, pp. 2419-2431.

* cited by examiner

*Primary Examiner* — Terry A Mckelvey
*Assistant Examiner* — Jacob A Boeckelman
(74) *Attorney, Agent, or Firm* — Revolution IP, PLLC

(57) ABSTRACT

The present invention provides a pharmaceutical composition and health functional food composition for preventing or treating female menopausal disease including extract of *Ribes fasciculatum* leaves as an active ingredient, and a pharmaceutical composition and health functional food composition for preventing or treating female menopausal disease including an extract of *Cornus officinalis* and extract of *Ribes fasciculatum* leaves as active ingredients.

3 Claims, 11 Drawing Sheets

COMPOSITION FOR PREVENTING, IMPROVING OR TREATING FEMALE MENOPAUSAL DISEASE

CROSS-REFERENCE TO RELATED APPLICATION

This Applications claims priority to and the benefit of Korean Patent Application No. 10-2019-0023859 filed in the Korean Intellectual Property Office on Feb. 28, 2019, the entire contents of which are incorporated herein by reference.

BACKGROUND OF THE DISCLOSURE

1. Field of the Disclosure

The present invention relates to a composition for preventing, improving or treating female menopausal diseases.

2. Description of the Related Art

Women's climacterium, also called menopause, refers to the period of transition from maturity to old age as a female in view of a function of the ovaries. The age of climacterium is statistically around 50 years old, although there are individual differences according to the physical constitution, nutritive conditions and number of deliveries. The menopause tends to be delayed slightly due to the prolongation of life expectancy. The onset of climacterium begins from the period of perimenopause, when the amount of estrogen begins to decrease, during menopause, the production of estrogen and progesterone is very low and menstruation is completely stopped, from about 12 months after menstruation has completely stopped, it is the postmenopausal period.

In Korea, the average age of menopause is 49.7 years, and about 50% of Korean women are known to have symptoms of acute female hormone deficiency including hot flashes and sweating. In some cases, treatments for osteoporosis due to persistent decrease in bone density and obesity due to hormonal decline are needed. The types and degree of climacteric symptoms vary widely from mild enough for daily life to severe enough to lie in sickbed according to individual differences, and about 30% of menopausal women are known to have been treated with severe symptoms.

Therefore, it is necessary to suggest management measures to alleviate menopausal symptoms and prevent the occurrence of chronic diseases, which are important factors that degrade the quality of life of women. The number of prescription drugs of Premarin and Prempro which are representative female hormones in the United States from 2000 to 2001, there were over 60 million, but the number of prescriptions dropped sharply in May 2002 after the US National Institutes of Health announced a side effect of breast cancer, stroke, and cardiovascular disease and accordingly in 2005, the figure decreased to one third compared to year 2000 to 2001.

On the other hand, health functional foods such as *Cynanchum wilfordii* Hemsley complex extract, pomegranate concentrate, and such as calcium, vitamin D, and isoflavone, which are good for bone, are used, but the effect thereof is limited. Therefore, there is a need for the development of pharmaceutical preparations or health functional foods for more effective prevention, improvement or treatment of female menopausal symptoms.

SUMMARY OF THE DISCLOSURE

1. Technical Problem

In order to solve the problems as described above, the present invention provides a pharmaceutical composition for preventing or treating female menopausal disease comprising extract of *Ribes fasciculatum* leaves.

The present invention provides a pharmaceutical composition for preventing or treating female menopausal disease comprising extract of *Cornus officinalis* and extract of *Ribes fasciculatum* leaves.

The present invention provides a health functional food composition for preventing or improving female menopausal disease comprising extract of *Ribes fasciculatum* leaves.

The present invention provides a health functional food composition for preventing or improving female menopausal disease comprising extract of *Cornus officinalis* and extract of *Ribes fasciculatum* leaves.

2. Technical Solution

The present invention provides a pharmaceutical composition for preventing or treating female menopausal disease comprising extract of *Ribes fasciculatum* leaves as an active ingredient.

The present invention provides a pharmaceutical composition for preventing or treating female menopausal disease comprising extract of *Cornus officinalis* and extract of *Ribes fasciculatum* leaves as active ingredients.

The present invention provides a health functional food composition for preventing or improving female menopausal disease comprising extract of *Ribes fasciculatum* leaves as an active ingredient.

The present invention provides a health functional food composition for preventing or improving female menopausal disease comprising extract of *Cornus officinalis* and extract of *Ribes fasciculatum* leaves as active ingredients.

BRIEF DESCRIPTION OF THE DRAWINGS

FIG. 10 is a flow chart showing a process of producing a mixed extract powder of *Cornus officinalis* and leaves of *Ribes fasciculatum* according to an embodiment of the present invention.

FIG. 4A shows an extracted uterus of the mouse, FIG. 4B shows a dyed cut surface of the uterus and FIG. 4C is a graph comparing the weight of the uterus.

FIG. 5A shows a stained adipose tissue of the liver and FIG. 5B shows a stained adipose tissue of the abdomen.

FIG. 6A is a graph showing the weight of the menopausal mouse model, FIG. 6B is a graph showing the body fat percentage of the menopausal mouse model, FIG. 6C is a graph showing the weight of the obese mouse model and FIG. 6D is a graph showing the body fat percentage of the obese mouse model.

FIG. 7A is a graph showing the bone density of the femoral region, FIG. 7B is a graph showing the mineral content of the femoral region and FIG. 7C is a microscopic image of an extracted femoral region by micro-CT.

DETAILED DESCRIPTION OF THE EMBODIMENTS

Figure 1A:
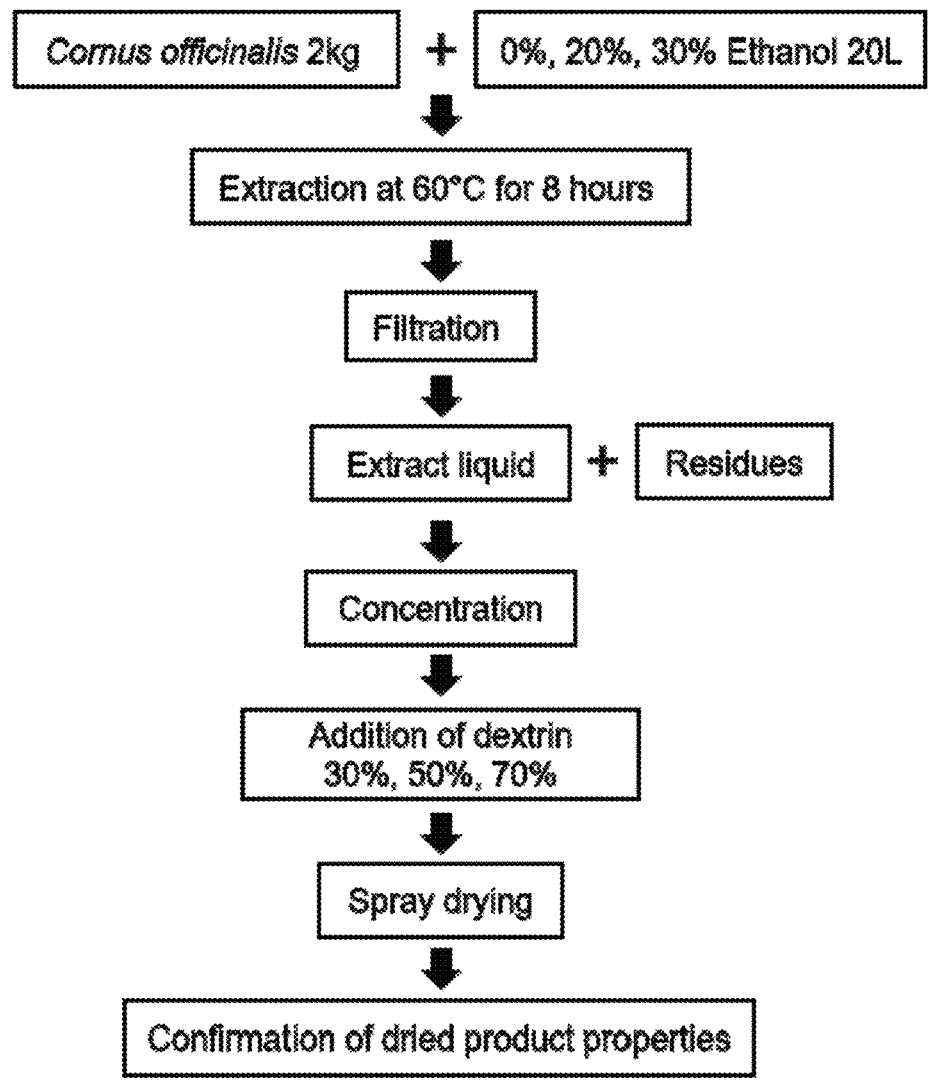
FIG. 1A is a flow charts showing a process of producing extract powder of *Cornus officinalis* according to an embodiment of the present invention.

Hereinafter, the present invention will be described in detail.

The present inventors have confirmed that extract of *Ribes fasciculatum* leaves or a mixed extract of *Cornus officinalis* and leaves of *Ribes fasciculatum* has the efficacy in decreased estrogen hormone in menopausal women and osteoporosis, weight gain and improvement of fat accumulation and fat cell size increase in liver and abdominal adipose tissue, which are associated with decreased estrogen hormone in menopausal women and completed the present invention.

As used herein, "*Ribes fasciculatum*" is a summergreen shrub belonging to Saxifragaceae, which grows under the trees of mountain valleys in Korea, Japan, and northeastern China and can be used interchangeably as '*Ribes fasciculatum* var. *chinense* Maxim.', '*Ribes fasciculatum* var. *chinense*'.

As used herein, "*Cornus officinalis*" is an oval fruit of a *cornus* tree, which is a deciduous tree belonging to Cornaceae and is known to have a warm, sour and astringent taste and no toxicity.

As used herein, the term "extract" refers to a substance obtained by extracting a component of a natural product regardless of an extraction method, an extraction solvent, an extracted component or a form of extract, and may include all materials that can be obtained by extracting the components of natural products and then processing the materials by other methods.

As used herein, "prevention" refers to any action that inhibits or delays the development of female menopausal disease or at least one symptom of the disease by administering a pharmaceutical composition or a health functional food composition according to the present invention. Also included are treatments of subjects in remission of the disease in order to prevent a recurrence.

As used herein, "treatment" refers to any action that improves or beneficially alters the symptoms, such as alleviating, reducing, or eliminating female menopausal disease or at least one symptom of the disease by administering a pharmaceutical composition according to the present invention.

As used herein, the term "improvement" refers to any action that improves or beneficially alters the symptoms, such as alleviating, reducing, or eliminating female menopausal disease or at least one symptom of the disease by ingesting a health functional food composition according to the present invention.

As used herein, the term "pharmaceutical composition" means a composition administered for a specific purpose to prevent or treat female menopausal disease or at least one symptom of the disease for the purpose of the present invention.

As used herein, "health functional food" means foods manufactured and processed using raw materials or ingredients having functional properties useful to the human body, and foods having high medical and medicinal effects processed to efficiently exhibit bioregulatory functions in addition to nutrition supply and it can be used interchangeably with terms known in the art such as functional foods.

The present invention provides a pharmaceutical composition for preventing or treating female menopausal disease comprising extract of *Ribes fasciculatum* leaves as an active ingredient.

Also, the present invention provides a pharmaceutical composition for preventing or treating female menopausal disease comprising an extract of *Cornus officinalis* and extract of *Ribes fasciculatum* leaves as active ingredients.

In the pharmaceutical composition according to the present invention, the extract of *Ribes fasciculatum* leaves and the extract of *Cornus officinalis* are extracted with a solvent of a C1 to C4 alcohol or an aqueous solution thereof. For example, methanol or ethanol aqueous solution can be used as an extraction solvent.

According to an embodiment of the present invention, the extract of *Ribes fasciculatum* leaves was prepared by extracting leaves of *Ribes fasciculatum* which can be used for food, using 10 to 20 weight %, preferably 20 weight % of an ethanol aqueous solution as an extraction solvent under optimum condition such as at 60 to 80° C., preferably at 60° C. for 6 to 10 hours, preferably for 8 hours. The extract of *Cornus officinalis* was also prepared by extracting *cornus* fruits using 5 to 10 weight %, preferably 10 weight % of an ethanol aqueous solution as a solvent under optimum condition such as at 60 to 80° C., preferably at 60° C. for 6 to 10 hours, preferably for 8 hours.

The pharmaceutical composition according to the present invention may include a single extract of extract of *Ribes fasciculatum* leaves as an active ingredient, and a complex extract obtained by mixing and extracting an extract of *Cornus officinalis* and extract of *Ribes fasciculatum* leaves as active ingredients, or include a mixture of the extract of *Cornus officinalis* and the extract of *Ribes fasciculatum* leaves as active ingredients. At this time, the extract of *Cornus officinalis* and the extract of *Ribes fasciculatum* leaves may be mixed in a weight ratio of 6:4 to 8:2, preferably in a weight ratio of 7:3. According to one embodiment of the present invention, the extract was prepared by mixing the extract concentrate of *Cornus officinalis* and the extract concentrate of *Ribes fasciculatum* leaves in a weight ratio of 7:3.

In the pharmaceutical composition according to the present invention, the female menopausal disease may include a symptom due to the lowered estrogen secretion. Estrogen, a representative female hormone, refers to hormones such as estrone (E1), estradiol (E2) and estriol (E3), and the estradiol shows the strongest activity among the estrogens.

In addition, the female menopausal disease may include diseases occurring in not only menopausal women due to menopause, but also estrogen deficient patients due to other causes such as ovariectomy or ovarian dysfunction.

According to an experimental example of the present invention, the extract showed an effect of increasing the production of estradiol (17β-estradiol, E2) in the menopausal cell model and inhibiting the reduction of blood estradiol in the menopausal animal model.

In the pharmaceutical composition according to the present invention, the female menopausal disease may be at least one selected from the group consisting of contraction or degeneration of uterus, fatty liver, abdominal obesity, weight gain, osteoporosis, hot flashes, sweating, insomnia, nervousness, depression, dizziness, lack of concentration, short-term memory disorders, anxiety, memory loss, palpitations, myalgia, joint pain, skin dryness, vaginal dryness, vaginal atrophy, lower urethral atrophy, vaginitis, cystitis, urination pain, urination, hyperlipidemia and arteriosclerosis, but it is not limited thereto.

When climacterium begins, the ovarian hypofunction and malfunction reduces the female hormone secreted in the ovary, resulting in various symptoms. Menstrual cycles, menstrual periods, menstrual flow become irregular, and hot flashes appear mainly on the face and upper body, and sweating and chest palpitations occur. The atrophy of the genitals such as dry vulva and reduced vaginal mucus secretion can lead to increased frequency of urination or pain during urination. Other symptoms may include dizziness, tinnitus, high blood pressure, digestive problems, headaches, sleep disorders, memory loss, cognitive dysfunction, mood changes, and depression.

In addition, when menopause, calcium is released from the bones, which weakens the bones, so there may be low back pain or other pains in the bone system and can be easily fractured. Since estrogen is involved in stimulating and developing muscles in the uterus, a significant decrease in the estrogen receptor of uterine tissue cells is shown by estrogen reduction.

Estrogen receptors are activated by estradiol (17β-estradiol, E2) and a significant decrease in estrogen receptors causes contraction and degeneration of the uterus. In addition, new estrogens are generated from fat cells of adipose tissue to offset estrogen deficiency, and more fat cells are produced in this process, which may cause abdominal obesity.

According to an experimental example of the present invention, the extract of *Cornus officinalis* and extract of *Ribes fasciculatum* leaves have improved the uterine contraction and degeneration, fat accumulation in liver and fat cell size in abdominal adipose tissue and inhibited the weight gain, the increase of body fat percentage and the decrease of the bone density or the mineral content. Therefore, the above extract can be used as an active ingredient of the pharmaceutical composition for preventing or treating the female menopausal disease. More details will be described later in Experimental Examples.

The pharmaceutical composition according to the present invention may be prepared according to conventional methods in the pharmaceutical art.

The pharmaceutical composition according to the present invention may be combined with a suitable pharmaceutically acceptable carrier according to the above formulation, and, if necessary, further includes excipients, diluents, dispersants, emulsifiers, buffers, stabilizers, binders, disintegrants, solvents, and the like. The term "pharmaceutically acceptable" means materials which have no toxicity to the cells or humans exposed to the pharmaceutical composition and the appropriate carrier, etc. does not inhibit the activity and properties of the extract according to the present invention and it may be chosen differently depending on the administration route and the formulation.

The pharmaceutical composition according to the present invention may be applied in any formulation form, and more specifically, may be used by formulating as oral formulations and parenteral formulations such as external preparations, suppositories and sterile injectable solutions according to conventional methods.

Solid formulations for the oral administration include tablets, pills, powders, granules, capsules, etc., and such solid formulations may contain at least one excipient such as starch, calcium carbonate, sucrose, lactose, sorbitol, mannitol, cellulose, gelatin and the like and in addition to simple excipients, lubricants such as magnesium stearate and talc are also included. In addition, the capsule formulation may further include a liquid carrier such as fatty oil in addition to the aforementioned substances.

In the pharmaceutical composition according to the present invention, the extract may be prepared in dry powder form using an excipient. According to an embodiment of the present invention, the extract of *Ribes fasciculatum* leaves may be prepared in powder form by adding 0 to 50 weight % of dextrin, preferably 30 weight % of dextrin as an excipient followed by spray drying. The extract of *Cornus officinalis* may be prepared in powder form by adding 30 to 70 weight % of dextrin, preferably 70 weight % of dextrin as an excipient followed by spray drying. In addition, when the extract of *Cornus officinalis* and extract of *Ribes fasciculatum* leaves are mixed, it can be prepared in a powder form by adding 40 to 60 weight %, preferably 50 to 55 weight % of dextrin. Among the oral formulations, liquid formulations include suspensions, oral solutions, emulsions, and syrups, and may include various excipients such as wetting agents, sweeteners, fragrances, preservatives and the like in addition to commonly used simple diluents such as water and liquid paraffin.

Formulations for parenteral administration include sterile aqueous solutions, non-aqueous solvents, suspensions, emulsions, freeze drying agents, suppositories. As the non-aqueous solvents and suspensions, propylene glycol, polyethylene glycol, vegetable oils such as olive oil, injectable esters such as ethyl oleate, and the like may be used. As the base of the suppository, witepsol, macrogol, tween 61, cacao butter, laurinum, glycerogelatin and the like may be used. Without limitation thereto, any suitable agent known in the art may be used.

In addition, the pharmaceutical composition according to the present invention may further add calcium or vitamin $D_3$ and the like to enhance the therapeutic efficacy.

In the pharmaceutical composition according to the present invention, the pharmaceutical composition may be administered in a pharmaceutically effective amount. The term "pharmaceutically effective amount" means an amount sufficient to treat a disease at a reasonable benefit/risk ratio applicable to medical treatment and not causing side effects.

The effective dosage level of the pharmaceutical composition is determined by factors including the intended use, age, sex, weight and health condition of the patient, type and severity of disease, drug activity, sensitivity to the drug, method and time of administration, route of administration and rate of release, treatment duration, drugs used in combination or simultaneously and other factors well known in the medical field. For example, although not constant, generally from 0.001 to 100 mg/kg, preferably 0.01 to 10 mg/kg may be administered once to several times daily. The dosage does not limit the scope of the invention in any aspect.

The pharmaceutical compositions according to the invention can be administered by any suitable route of administration depending on the form of preparation and can be administered via various routes of oral or parenteral, as long as it can reach the target tissue. The method of administration need not be particularly limited and may be administered by conventional methods, for example, oral, rectal or intravenous, intramuscular, subcutaneous, intrabronchial inhalation, intrauterine dural or intracerebroventricular injection.

The pharmaceutical composition according to the present invention may be used alone for preventing or treating female menopausal diseases, and may be used in combination with surgery or other medicine treatment and the like.

The present invention provides a health functional food composition for preventing or improving female menopausal disease comprising extract of *Ribes fasciculatum* leaves as an active ingredient.

In addition, the present invention provides a health functional food composition for preventing or improving female menopausal disease comprising an extract of *Cornus officinalis* and extract of *Ribes fasciculatum* leaves as active ingredients.

In the health functional food composition according to the present invention, the extract may be prepared by the same method as the above method of preparing the extract which is an active ingredient of the above-described pharmaceutical composition.

Health functional food composition according to the present invention may include a single extract of extract of *Ribes fasciculatum* leaves as an active ingredient, and a complex extract obtained by mixing and extracting an extract of *Cornus officinalis* and extract of *Ribes fasciculatum* leaves as active ingredients, or include a mixture of the extract of *Cornus officinalis* and the extract of *Ribes fasciculatum* leaves as active ingredients. At this time, the extract of *Cornus officinalis* and the extract of *Ribes fasciculatum* leaves may be mixed in a weight ratio of 6:4 to 8:2, preferably in a weight ratio of 7:3. According to one embodiment of the present invention, the extract was prepared by mixing the extract concentrate of *Cornus officinalis* and the extract concentrate of *Ribes fasciculatum* leaves in a weight ratio of 7:3.

In the food functional food composition according to the present invention, the female menopausal disease may include a symptom due to the lowered estrogen secretion and may also include diseases occurring in not only menopausal women due to menopause, but also estrogen deficient patients due to other causes such as ovariectomy or ovarian dysfunction.

According to an experimental example of the present invention, the extract showed an effect of increasing the production of estradiol (17β-estradiol, E2) in the menopausal cell model and inhibiting the reduction of blood estradiol in the menopausal animal model.

In the health functional food composition according to the present invention, the female menopausal disease may be at least one selected from the group consisting of contraction or degeneration of uterus, fatty liver, abdominal obesity, weight gain, osteoporosis, hot flashes, sweating, insomnia, nervousness, depression, dizziness, lack of concentration, short-term memory disorders, anxiety, memory loss, palpitations, myalgia, joint pain, skin dryness, vaginal dryness, vaginal atrophy, lower urethral atrophy, vaginitis, cystitis, urination pain, urination, hyperlipidemia and arteriosclerosis, but it is not limited thereto.

According to an experimental example of the present invention, the extract of *Cornus officinalis* and extract of *Ribes fasciculatum* leaves have improved the uterine contraction and degeneration, fat accumulation in liver and fat cell size in abdominal adipose tissue and inhibited the weight gain, the increase of body fat percentage and the decrease of the bone density or the mineral content decrease. Therefore, the above extract can be used as an active ingredient of the health function food composition for preventing or improving the female menopausal disease. More details will be described later in Experimental Examples.

In the health functional food composition according to the present invention, the health functional food may be prepared in powder, granules, tablets, capsules, syrups or beverages, and the like, and as long as the health functional food can be produced, there is no limitation in the form, and it may include all foods of the usual meaning. For example, it may include beverages and various drinks, fruits and processed foods thereof (canned fruits, jams, etc.), fish, meat and processed foods thereof (ham, bacon, etc.), breads and noodles, cookies and snacks, dairy products (butters, cheeses, etc.) and the like, and all the functional foods in a conventional sense.

The health functional food composition according to the present invention may be prepared by further comprising sitologically acceptable food additives and other suitable auxiliary ingredients conventionally used in the art. For example, it may further contain flavors, natural carbohydrates, sweeteners, vitamins, electrolytes, colorants, pectic acids, alginic acids, organic acids, protective colloidal thickeners, pH adjusters, stabilizers, preservatives, glycerin, alcohols, carbonating agents and the like. In particular, as the natural carbohydrate, monosaccharides such as glucose and fructose, disaccharides such as maltose and sucrose, polysaccharides such as dextrin and cyclodextrin, sugar alcohol such as xylitol, sorbitol and erythritol can be used. Examples of the flavoring agents include natural sweeteners such as thaumatin and stevia extract or synthetic sweeteners such as saccharin and aspartame and the like.

The health functional food composition according to the present invention is a food as a raw material unlike the general medicine and thus it has the advantage that there are no side effect that can occur when taking a long-term use of the drug, excellent portability and thus it can be ingested as a supplement for preventing or improving female menopausal diseases.

Hereinafter, examples of the present invention will be described in detail to understand the present invention. The present invention may, however, be embodied in many different forms and should not be limited to the embodiments set forth herein in order to clearly illustrate the present invention for those skilled in the art to which the present invention pertains.

<Example 1> Method of Preparing Extract Powder of *Cornus officinalis*, Extract Powder of *Ribes fasciculatum* Leaves and Mixture Thereof Firstly, an extract powder of *Cornus officinalis* and an extract powder of *Ribes fasciculatum* leaves were prepared.

FIG. 1 is flow charts showing a process of producing extract powder of *Cornus officinalis* (1a), a process of producing extract powder of *Ribes fasciculatum* leaves (1b) and a process of producing a mixed extract powder of *Cornus officinalis* and *Ribes fasciculatum* leaves (1c) according to an embodiment of the present invention.

Figure 1B:
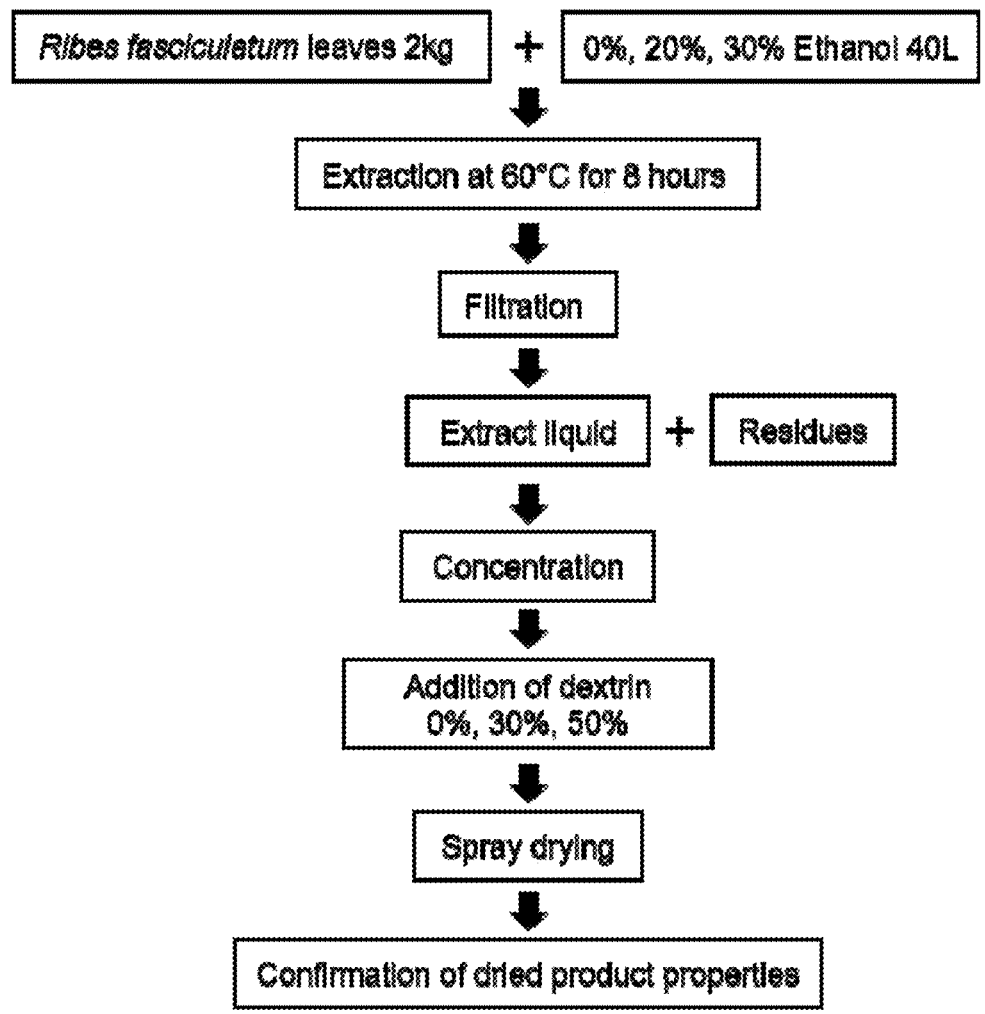
FIG. 1B is a flow chart showing a process of producing extract powder of *Ribes fasciculatum* leaves according to an embodiment of the present invention.

Referring to FIG. 1a and FIG. 1b, raw materials of *Cornus officinalis* and *Ribes fasciculatum* leaves were extracted with 0% of ethanol (water extraction), 20% and 30% of ethanol for 8 hours at 60° C. and 20% and 30% of ethanol were selected as the optimal condition for extraction of *Cornus officinalis* and *Ribes fasciculatum* leaves, respectively. The test of *Cornus officinalis* was performed in 30%, 50% and 70% of dextrin, the excipient used for powdering through spray drying and that of leaves of *Ribes fasciculatum* was performed in 0%, 30% and 50% of the dextrin. The optimal contents of dextrin were 70% in *Cornus officinalis* and 30% in leaves of *Ribes fasciculatum*.

Figure 1C:
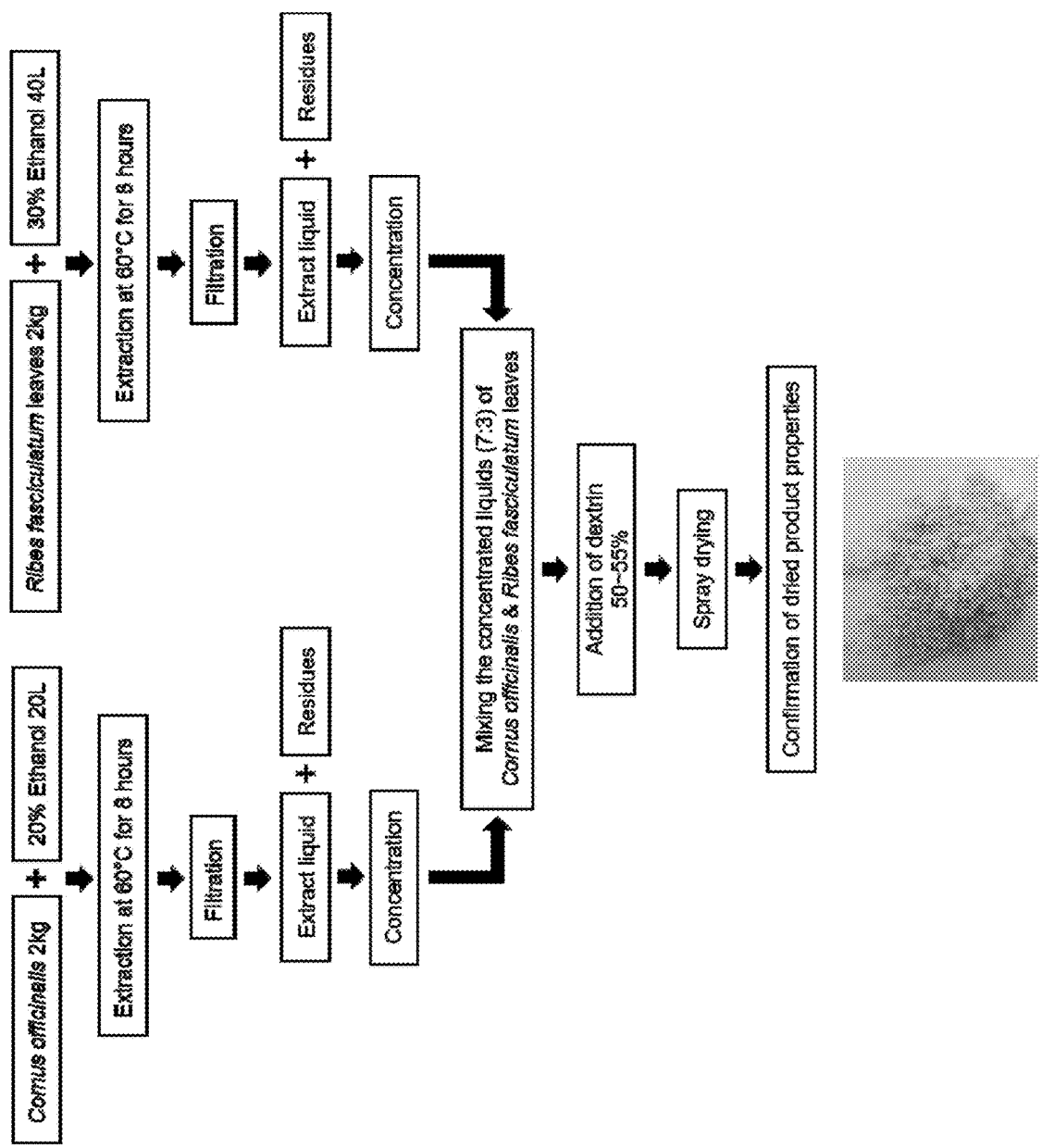

Referring to FIG. 1c, the mixed extract powder of *Cornus officinalis* and leaves of *Ribes fasciculatum* was prepared by mixing the concentrated liquids of *Cornus officinalis* and leaves of *Ribes fasciculatum* at 7:3 weight ratio, considering the manufacturing conditions and the optimum content of the excipient (dextrin) used for powdering through spray drying was 50 to 55%. In the case of *Cornus officinalis* extract powder, it was excluded from further experiments because the optimum content of excipient (dextrin) was very high (70%) and thus had low possibility of commercialization. Therefore, all the experiments including the following Experimental Example 1 were carried out using the extract powder of leaves of *Ribes fasciculatum* prepared in Example 1 and the mixed extract powder of *Cornus officinalis* and leaves of *Ribes fasciculatum* (7:3).

<Experimental Example 1> Menopausal Cell Model Experiment

Experiments on the menopausal cell model have been performed to analyze the production amount of estradiol by ELISA by treating estradiol (follicle hormone) precursor, androstenedione (ADD) to ovarian granulosa cells (COV434 granulosa cells).

COV434 cells were incubated at 37° C. for 4 days in succession at a density of $5 \times 10^5$ cells/well in a 12-well microplate. The cells were treated with androstenedione at a concentration of 10 μM alone or treated with an extract powder of *Cornus officinalis*, an extract powder of *Ribes fasciculatum* leaves and a mixed extract powder of *Cornus officinalis* and leaves of *Ribes fasciculatum* according to Example 1 and were incubated at 37° C. for 18 hours. The amount of estradiol in the cell culture was measured using an ELISA kit.

Figure 2:
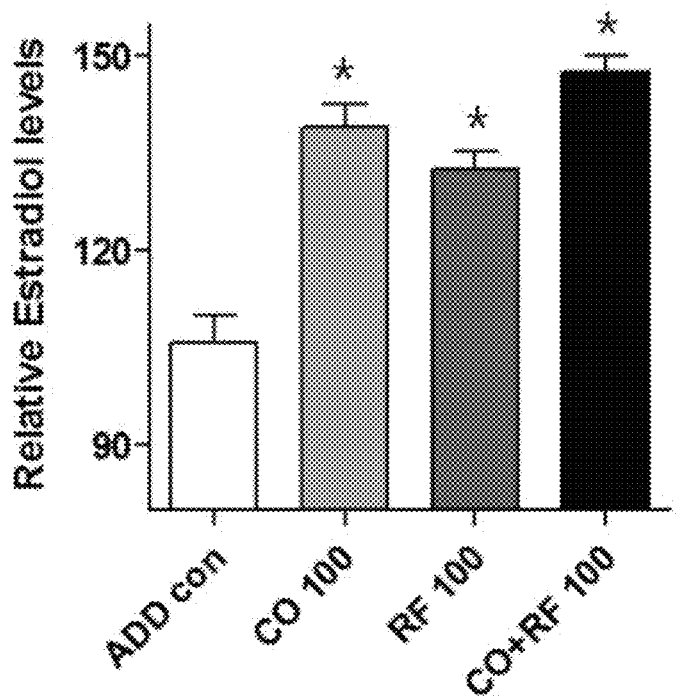
FIG. 2 is a graph showing the amount of estradiol produced in the cell model according to an experimental example of the present invention.

FIG. 2 is a graph showing the amount of estradiol produced in the cell model according to an experimental example of the present invention.

Referring to FIG. 2, 'ADD con' is a control group treated with androstenedione (hereinafter, ADD) alone, 'CO 100' is ADD+*Cornus officinalis* extract 100 μg/ml treatment group, 'RF 100' is ADD+*Ribes fasciculatum* leaves extract 100 μg/ml treatment group, 'CO+RF 100' is ADD+mixed extract of *Cornus officinalis* and *Ribes fasciculatum* leaves 100 μg/ml treatment group, compared to the control group treated with ADD alone, all the groups treated with other extracts showed significant increases in estradiol production (* $p<0.05$ vs ADD con).

<Experimental Example 2> Menopausal and Obese Animal Model Experiment

In order to evaluate the in vivo efficacy of the extract using a mixed extract powder of *Cornus officinalis* and leaves of *Ribes fasciculatum* according to the Example 1, a 10-week-old ovariectomized ddY female mouse (OVX mouse) was used as a menopausal animal model. The mouse was further bred for 2 weeks for surgical recovery after the ovariectomy at 8 weeks of age. As a control group, the group of shame mice (normal control group) with laparotomy but without ovariectomy and the group of OVX mice (negative control group) administered physiological saline only to ovariectomzed mice were used. Eight-week-old sham-operated mice and ovariectomzed ddY female mice were purchased from Central Experimental Animals Co., Ltd. and after 2 weeks of acclimation in the quarantine room of Ajou University Experimental Animal Center, they were transferred to the clean animal breeding area.

Obese animal models were 4-week-old C57BL6J mice, and high fat diet (HFD) diet was used to induce obesity. The weight of each mouse was measured, and group separation was performed so that there was no statistically significant weight difference between the experimental groups. The mixed extract powder of *Cornus officinalis* and leaves of *Ribes fasciculatum* for the experiment was prepared by mixing it with feed and it was sterilized by gamma-ray irradiation from Soya Greentec Co., Ltd.

The mixed extract of *Cornus officinalis* and *Ribes fasciculatum* leaves of 75 mg/kg/day (CO+RF(L), low concentration), 150 mg/kg/day (CO+RF(M), medium concentration), 300 mg/kg/day (CO+RF(H), high concentration) were ingested in the experimental group for 12 weeks, blood estrogen concentration, uterine tissue size, weight, fat cell size of liver and abdominal adipose tissue were measured and analyzed. Bone mineral density, bone mineral content and micro-CT were measured.

1. Confirmation of improved estrogen reduction effect of mixed extract of *Cornus officinalis* and *Ribes fasciculatum* leaves in female menopausal mouse model.

A common female menopausal symptom is a marked decrease in the female hormones, estrogen and progesterone. Twelve weeks after the administration of the mixed extracts of *Cornus officinalis* and *Ribes fasciculatum* leaves to a female menopausal mouse model, serum was isolated from mouse blood and the amount of estrogen estradiol (17β-estradiol, E2) in the blood was measured using the ELISA method.

Figure 3:
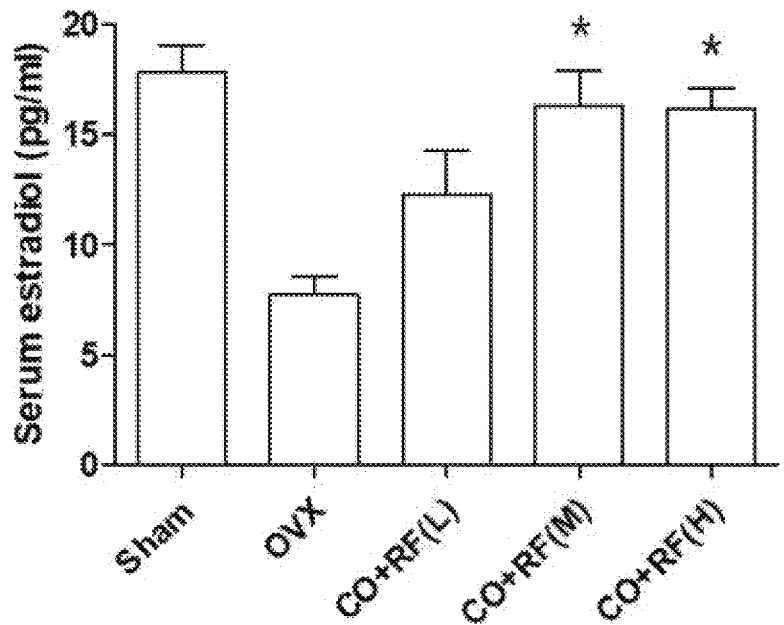
FIG. 3 is a graph showing the amount of estradiol in blood in a mouse model according to an experimental example of the present invention.

FIG. 3 is a graph showing the amount of estradiol in the blood in a mouse model according to an experimental example of the present invention.

Referring to FIG. 3, estradiol, a female hormone, was markedly reduced in OVX mice with ovariectomy compared to normal shame mice without ovariectomy. On the other hand, in the mixed extracts of *Cornus officinalis* and *Ribes fasciculatum* leaves administration group (CO+RF(L), CO+RF(M), CO+RF(H)), it was found that the reduction of estradiol, a female hormone, in the blood was suppressed and the inhibitory effect of blood estradiol reduction was larger in the mixed extracts of *Cornus officinalis* and *Ribes fasciculatum* leaves at the medium concentration and higher. Statistical analysis also confirmed the significance of the efficacy (*:$p<0.05$ vs. OVX negative control).

2. Confirmation of improved uterine contraction and degeneration of mixed extract of *Cornus officinalis* and *Ribes fasciculatum* leaves in female menopausal mouse model.

A common menopausal symptom includes contraction and degeneration of the uterus due to estrogen reduction. Twelve weeks after the administration of the mixed extracts of *Cornus officinalis* and *Ribes fasciculatum* leaves to a female menopausal mouse model, the uterus of the mouse was extracted and the shape, size, thickness and weight of the uterus were observed.

Figure 4A:
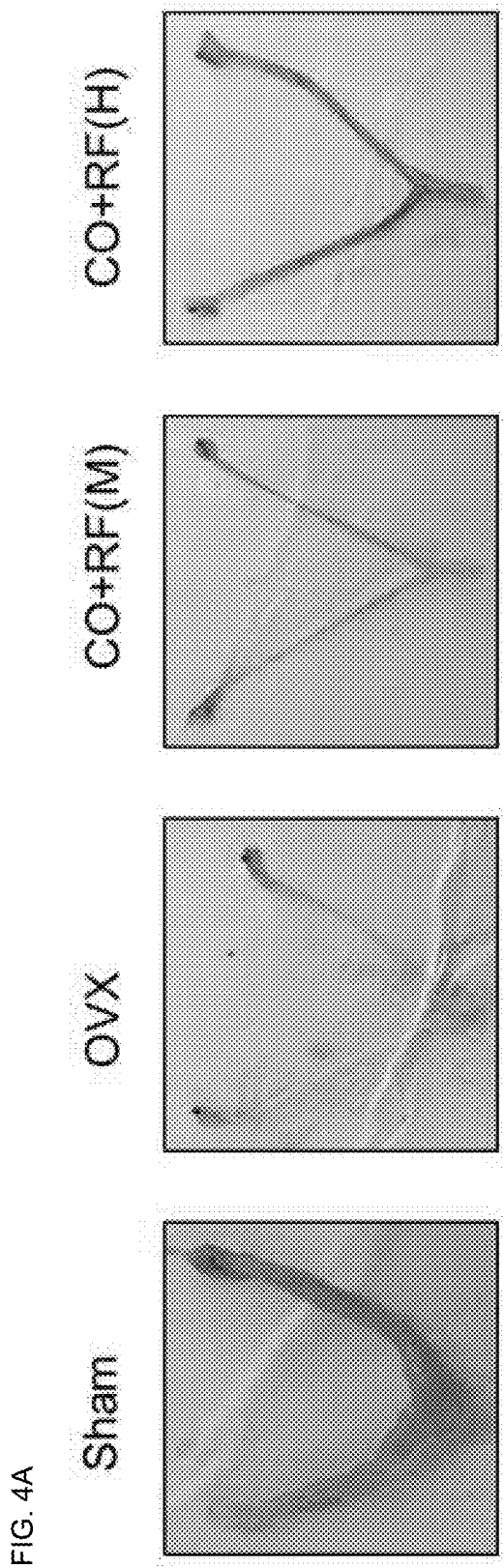
FIGS. 4A-4C shows photographs observing the uterus of the mouse model according to an experimental example of the present invention.
Figure 4B:
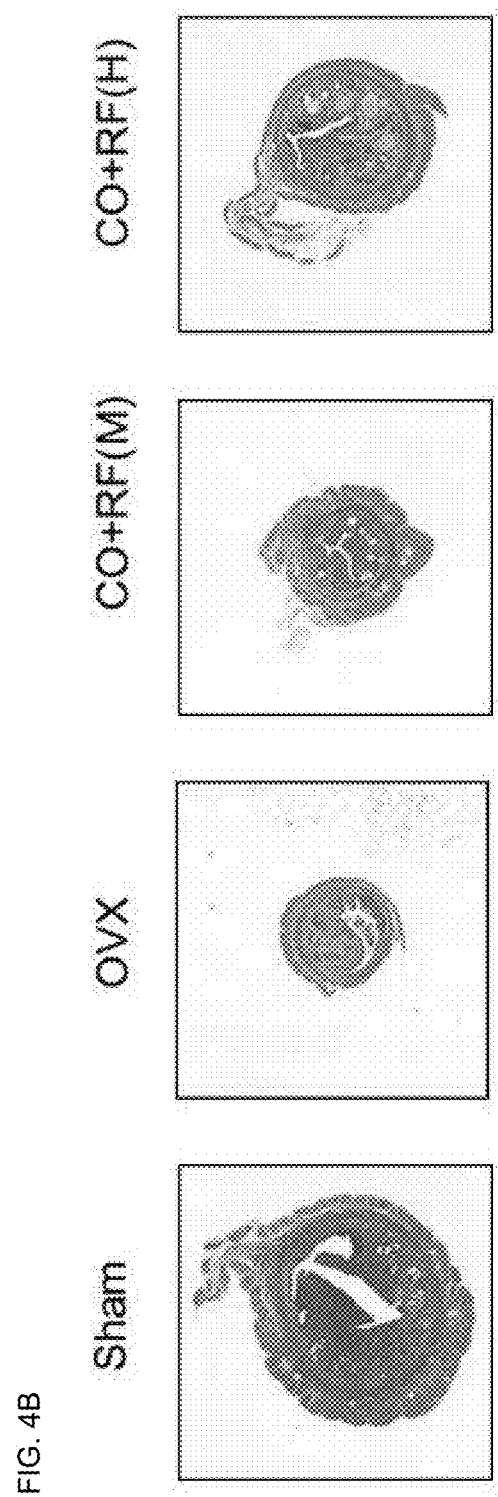
Figure 4C:
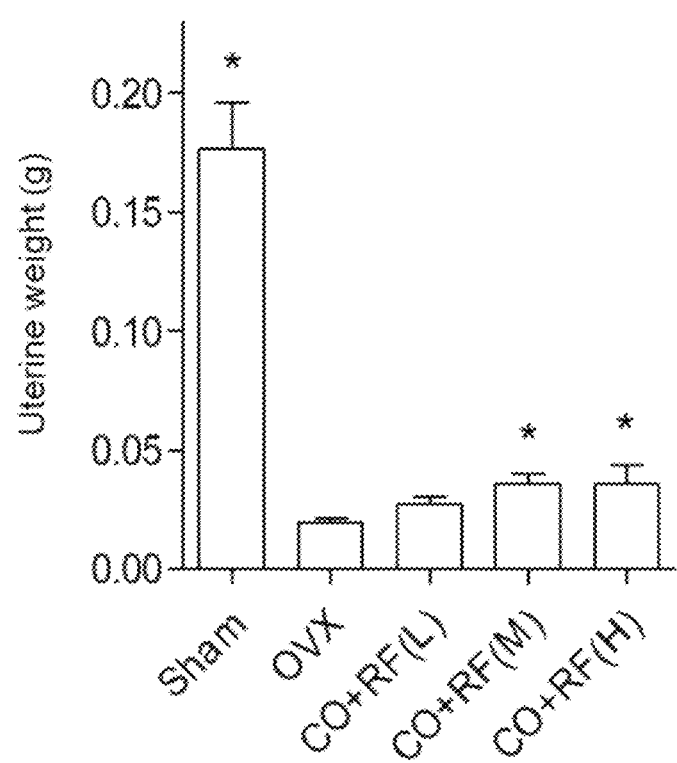

FIG. 4 shows photographs observing the uterus of the mouse model according to an experimental example of the present invention. FIG. 4a shows an extracted uterus of the mouse, FIG. 4b shows a dyed cut surface of the uterus and FIG. 4c is a graph comparing the weight of the uterus.

Referring to FIG. 4, when compared to normal shame mouse without ovariectomy, the uterus of OVX mouse with ovariectomy was contracted or degenerated showing a small and thin form, the thickness of the cut surface was thin, and the weight of the uterus was light. In contrast with the above, in the mixed extracts of Cornus officinalis and Ribes fasciculatum leaves administration group, the exterior shape and size of the uterus were larger and clearer than those of OVX mice, and the decrease in the thickness and the weight of the uterus on the uterine cutting surface stained with H&E staining using hematoxylin and eosin was found to be significantly suppressed. That is, it means that the mixed extract of Cornus officinalis and Ribes fasciculatum leaves has a significant effect on suppressing uterine contraction and degeneration due to menopause. The statistical analysis also confirmed the significance of the efficacy (*:p<0.05 vs. OVX negative control).

3. Confirmation of improved effect of mixed extracts of Cornus officinalis and Ribes fasciculatum leaves on fat accumulation in liver and fat cell size increase in abdominal adipose tissue in female menopausal mouse model.

In general, when estrogen is reduced in female menopause, new estrogens are produced from adipocytes to compensate for estrogen deficiency. In this process, more fat cells are produced, which may cause abdominal obesity, fat accumulation in the liver and fat cell size increase in abdominal fat tissue. Twelve weeks after the administration of the mixed extracts of Cornus officinalis and Ribes fasciculatum leaves, liver and abdominal adipose tissues of the mouse were extracted and stained with H&E.

Figure 5A:
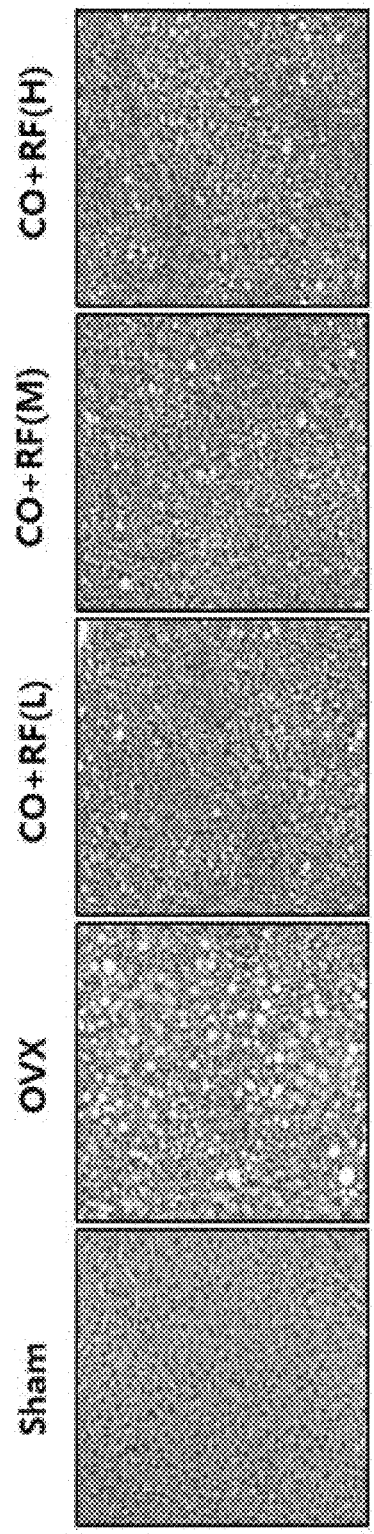
FIGS. 5A-5B shows photographs observing a change in adipocyte of the mouse model according to an experimental example of the present invention.
Figure 5B:
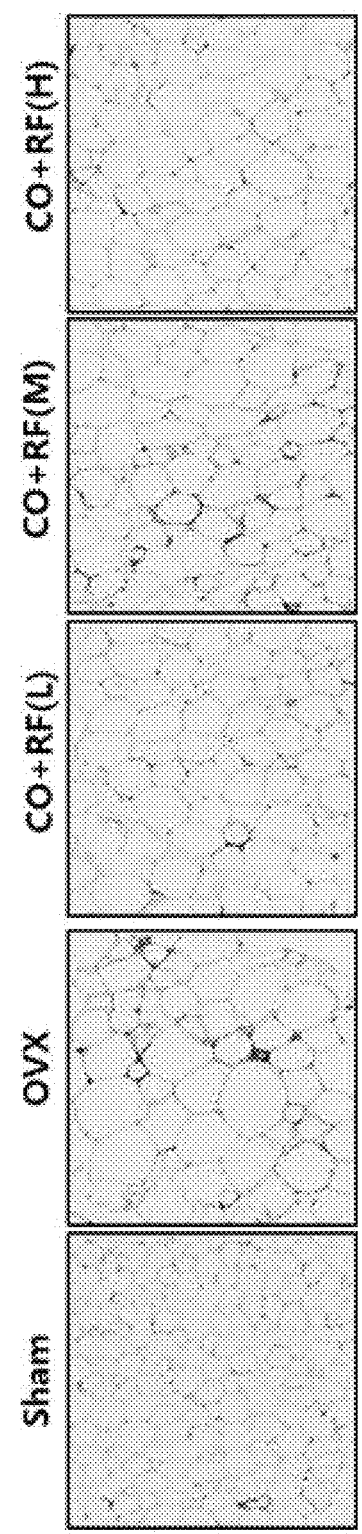
Figure 6A:
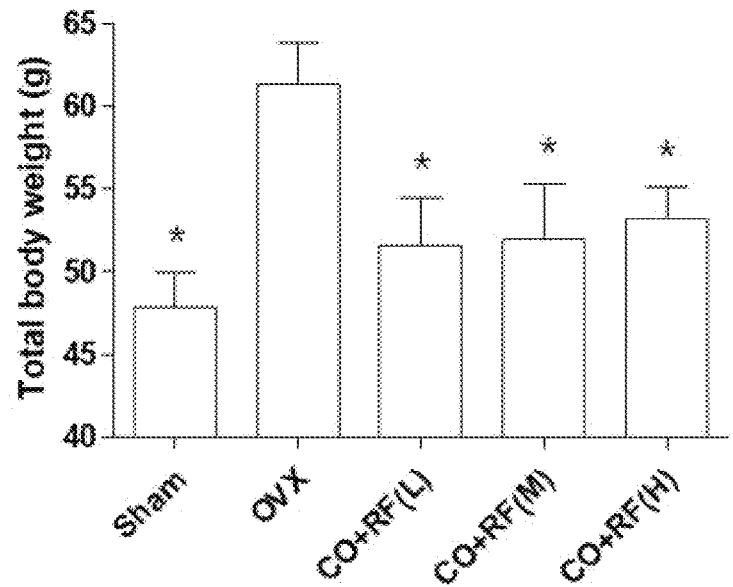
FIGS. 6A-6D are graphs illustrating a change in body weight of the mouse model according to an experimental example of the present invention.
Figure 6B:
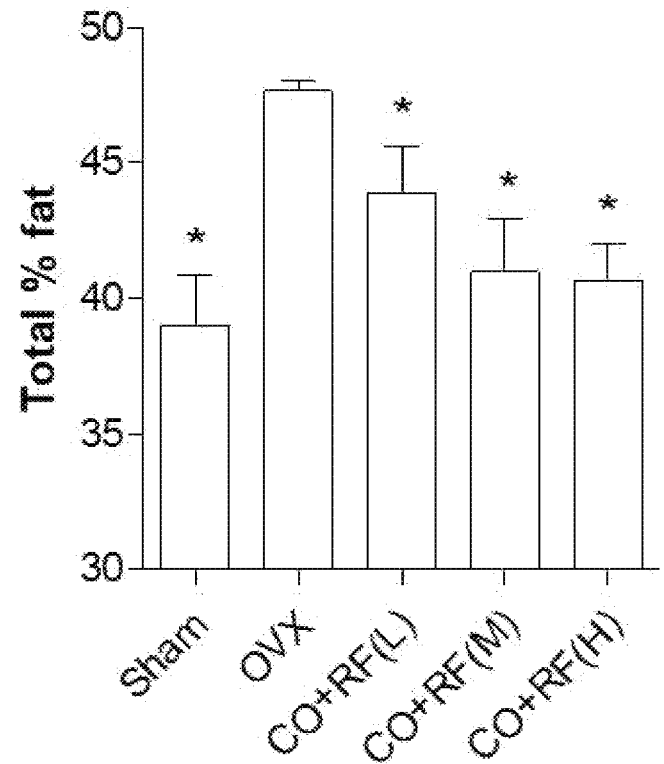
Figure 6C:
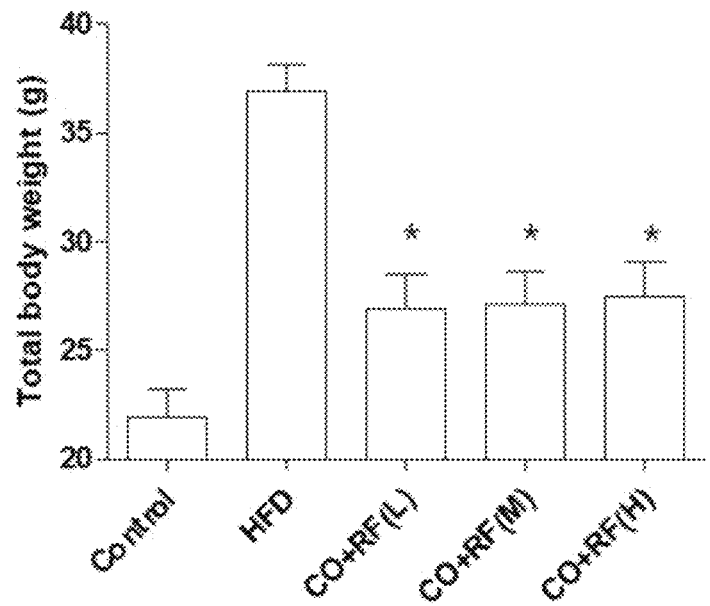
Figure 6D:
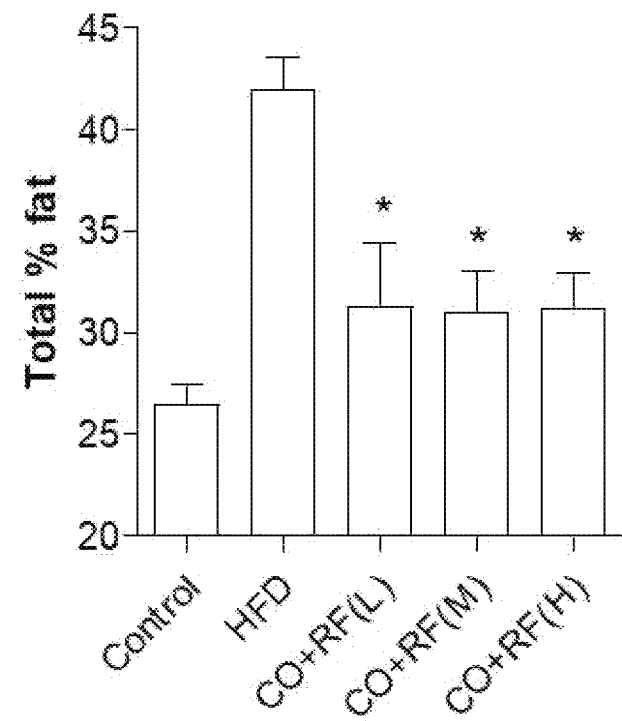

FIG. 5 shows photographs observing a change in adipocyte of the mouse model according to an experimental example of the present invention. FIG. 5a shows a stained adipose tissue of the liver and FIG. 5b shows a stained adipose tissue of the abdomen.

Referring to FIG. 5, the fat accumulation in the liver and the size of fat cells in abdominal adipose tissue was significantly increased of OVX mice with ovariectomy as compared with normal shame mice without ovariectomy. On the contrary, in the mixed extract of Cornus officinalis and Ribes fasciculatum leaves administration group, the accumulation of fat in the liver and the increase of fat cell size in abdominal adipose tissue were significantly suppressed. That is, it means that the mixed extract of Cornus officinalis and Ribes fasciculatum leaves has a significant suppression effect on the fat accumulation in the liver and the increase of fat cell size in abdominal adipose tissue caused by the menopause.

4. Confirmation of improved effect of mixed extracts of Cornus officinalis and Ribes fasciculatum leaves on weight gain in female menopausal and obese mouse models.

A common menopausal symptom includes weight gain due to estrogen reduction and obesity caused by high fat diet. A change in body weight and body fat percentage were measured after 12 weeks after the administration of the mixed extract of Cornus officinalis and Ribes fasciculatum leaves in female menopausal and obese mouse models.

FIG. 6 is a graph illustrating a change in body weight of the mouse model according to an experimental example of the present invention. FIG. 6a is a graph showing the weight of the menopausal mouse model, FIG. 6b is a graph showing the body fat percentage of the menopausal mouse model, FIG. 6c is a graph showing the weight of the obese mouse model and FIG. 6d is a graph showing the body fat percentage of the obese mouse model.

Referring to FIG. 6, the body weight and body fat percentage were significantly increased in OVX mice with ovariectomy and high fat diet-ingested mice (HFD) as compared with normal shame mice without ovariectomy. On the other hand, in the mixed extract of Cornus officinalis and Ribes fasciculatum leaves administration group, the increase of the weight and the body fat percentage of the menopausal mouse model and the obese mouse model was significantly suppressed. That is, it means that the mixed extract of Cornus officinalis and Ribes fasciculatum leaves has a significant effect of suppressing the weight gain and the fat percentage increase due to menopause and obesity. The statistical analysis also confirmed the significance of the efficacy (*:p<0.05 vs. OVX negative control, *:p<0.05 vs. HFD negative control).

5. Confirmation of osteoporosis improvement effects of mixed extract of Cornus officinalis and Ribes fasciculatum leaves in menopausal mouse model.

At the end of the menopausal animal experiments, the bone mineral density and the bone mineral content of the mouse femoral region were measured using a PIXI-mus bone densitometer, and femoral bones were extracted, and micro-CT was performed.

Figure 7A:
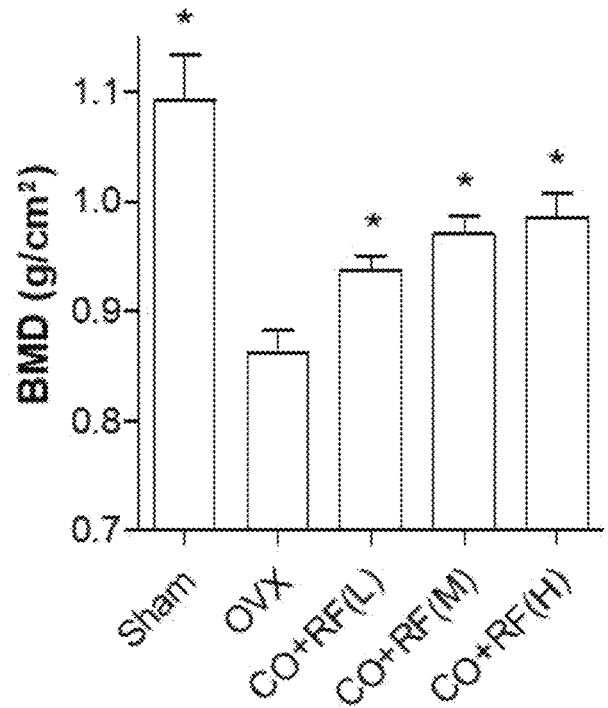
FIGS. 7A-7C are graphs showing a change in the femoral bones of the mouse model according to the present invention.
Figure 7B:
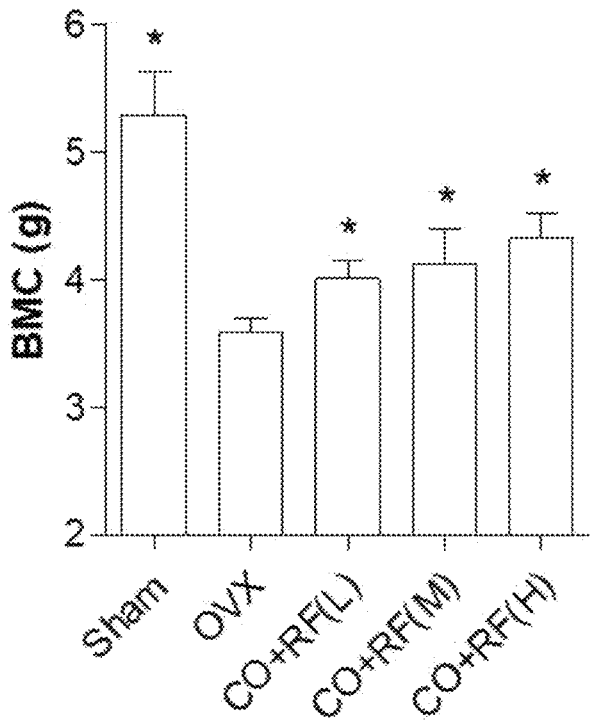
Figure 7C:
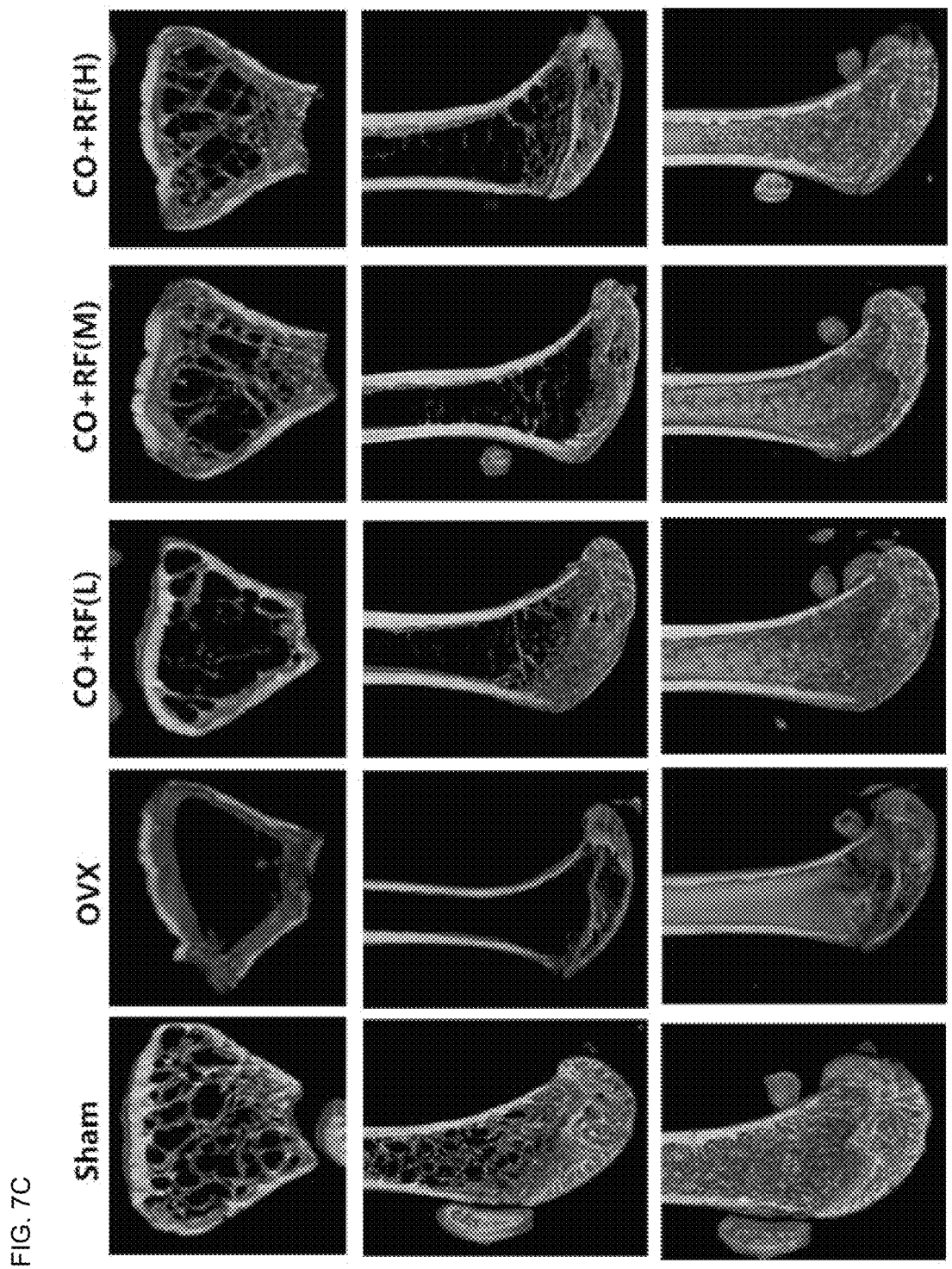

FIG. 7 is a graph showing a change in the femoral bones of the mouse model according to the present invention. FIG. 7a is a graph showing the bone density of the femoral region, FIG. 7b is a graph showing the mineral content of the femoral region and FIG. 7c is a microscopic image of an extracted femoral region by micro-CT.

Referring to FIG. 7, the bone density and the mineral content after 12 weeks of bone of OVX mice with ovariectomy were significantly reduced as compared to normal shame mice without ovariectomy, and also significant decrease the densification degree of bone microstructure was shown on micro-CT images. In contrast with the above, in the experimental group administered with the mixed extract of Cornus officinalis and Ribes fasciculatum leaves for 12 weeks, the decrease of the bone density and mineral content and the decrease of the densification degree of the bone microstructure by menopause were suppressed. In other words, it means that the mixed extract of Cornus officinalis and Ribes fasciculatum leaves has a significant effect of inhibiting the decrease of the bone density and mineral content and the decrease of the densification degree of the bone microstructure by menopause. In addition, the statistical analysis also confirmed the significance of the efficacy (*:p<0.05 vs. OVX negative control).

The extract of Ribes fasciculatum leaves or extract of Cornus officinalis and extract of Ribes fasciculatum leaves according to the present invention increases the production of female hormone estradiol in menopausal cell model and menopausal mouse mode, thereby having a significant effect in improving uterine contraction and degeneration, adipocyte accumulation and size in liver and abdominal adipose tissue, decreasing weight and body fat percentage and inhibiting bone loss.

By using the extract as a pharmaceutical composition or healthy functional food composition, it is possible to effectively prevent, improve or treat female menopausal diseases such as estrogen reduction, uterine contraction or degeneration, fatty liver, abdominal obesity, weight gain, osteoporosis, which can improve the quality of life for menopausal women.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

What is claimed is:

1. A method of preventing or treating female menopausal disease in a subject in need thereof, comprising:
   providing a pharmaceutical composition consisting of extract of *Cornus officinalis* and extract of *Ribes fasciculatum* leaves as active ingredients, wherein the pharmaceutical composition is obtained by mixing the extract of *Cornus officinalis* and the extract of *Ribes fasciculatum* leaves in a weight ratio of 6:4 to 8:2; and
   administering the pharmaceutical composition to the subject, wherein the female menopausal disease is prevented or treated, and the female menopausal disease is weight gain caused by a decrease in estrogen secretion.

2. A method of preventing or improving female menopausal disease in a subject in need thereof, comprising:
   providing a health functional food composition consisting of extract of *Cornus officinalis* and extract of *Ribes fasciculatum* leaves as active ingredients, wherein the health functional food composition is obtained by mixing the extract of *Cornus officinalis* and the extract of *Ribes fasciculatum* leaves in a weight ratio of 6:4 to 8:2; and
   administering the health functional food composition to the subject, wherein the female menopausal disease is prevented or improved, and the female menopausal disease is weight gain caused by a decrease in estrogen secretion.

3. The method of claim 1, wherein the extract is extracted with a solvent of a C1 to C4 alcohol or an aqueous solution thereof.

* * * * *